US005662110A

United States Patent [19]
Carr

[11] Patent Number: 5,662,110
[45] Date of Patent: Sep. 2, 1997

[54] MICROWAVE DETECTION APPARATUS FOR LOCATING CANCEROUS TUMORS PARTICULARLY BREAST TUMORS

[75] Inventor: Kenneth L. Carr, Harvard, Mass.

[73] Assignee: Microwave Medical Systems, Inc., Acton, Mass.

[21] Appl. No.: 627,117

[22] Filed: Apr. 3, 1996

[51] Int. Cl.$^6$ ............................................. A61B 5/00
[52] U.S. Cl. ........................................ 128/653.1; 128/736
[58] Field of Search ............................... 128/653.1, 736; 343/772, 703; 607/154

[56] References Cited

U.S. PATENT DOCUMENTS

| | | | |
|---|---|---|---|
| 3,778,837 | 12/1973 | Hardy | 343/703 |
| 4,162,500 | 7/1979 | Jacobi et al. | 343/772 |
| 4,428,382 | 1/1984 | Walsall et al. | 128/736 |
| 4,774,961 | 10/1988 | Carr | 128/736 |
| 4,815,479 | 3/1989 | Carr | 128/804 |
| 5,503,150 | 4/1996 | Evans | 128/653.1 |

*Primary Examiner*—Marvin M. Lateef
*Assistant Examiner*—Eleni Mantis Mercader
*Attorney, Agent, or Firm*—Cesari and McKenna

[57] ABSTRACT

Microwave tumor detection apparatus includes a probe having a working end arranged to contact tissue. Positioned in the probe is a plurality of rectangular waveguides arranged in columns and rows such that each waveguide has an aperture at the working end of the probe that is oriented substantially perpendicular to the aperture of the waveguide in any adjacent column and row of the array. The waveguides constitute antennas tuned to receive microwave radiation emitted by the tissue opposite the working end of the probe. The waveguides are coupled electrically and mechanically to dedicated radiometers in the probe for detecting the temperatures of tissue opposite the waveguides. These radiometers have thermally conductive casings which are mounted to a common heat sink and are insulated so that all of the radiometers have a uniform thermal distribution. Also, a thin thermally insulating interface pad may be located between the working end of the probe and the tissue contacted by the probe to prevent such contact from causing changes in the surface temperature of the tissue.

28 Claims, 4 Drawing Sheets

MICROWAVE DETECTION APPARATUS FOR LOCATING CANCEROUS TUMORS PARTICULARLY BREAST TUMORS

FIELD OF THE INVENTION

This invention relates to microwave detection apparatus. It relates especially to such apparatus suitable for screening for breast tumors.

BACKGROUND OF THE INVENTION

According to the American Cancer Society, approximately 180,000 American women were diagnosed with breast cancer in 1993. Approximately 45,400 died from the disease in the United States, breast cancer continues to be the most common of the nonpreventable cancers diagnosed among women. Much of the urgency in improving early diagnosis of breast cancer stems from the tragic and steady rise in the incidence of same ... 1 in 16 women in 1962, to 1 in 9 women in 1993. In fact, the incidences of breast cancer have been increasing steadily in the United States since formal tracking of cases through registries began in 1930. There has been no appreciable change in the death rate during the same period.

It has long been known that early detection of malignant tumors increases the chance of surival. In fact, the results of a 1976 National Institute of Heath Survey indicate a dramatic increase in survival (from 56% to 85%) as a result of early detection.

The technique that is used most often to screen for breast tumors is mammography. However, mammography exposes the patient to x-rays. This involves some hazard even though the radiation dosages are relatively small because multiple exposures of each breast are required in order to cover all quadrants of the breasts. Also, the procedure can be somewhat time consuming because the technician taking the mammogram is required to position the apparatus prior to taking each picture and then take refuge behind a leaded window while the x-ray tube is operative to avoid undo exposure to the radiation. Most importantly, mammography is disadvantaged because when adjusting the apparatus to the patient in order to obtain enough compression of the breast to ensure adequate x-ray penetration, the working end of the apparatus is often positioned so that the x-rays fail to properly illuminate the upper half of the breast and the axillary gland area above the upper outer quadrant of the breast where most tumors originate. This is particularly so for individuals with small breasts. Indeed, studies have shown that 80% of all breast tumors occur in the upper half of the breast and fully 69% arise in the upper outer quadrant of the breast and the axillary gland area. Resultantly, mammography misses many tumors.

Another technique for measuring tumors is thermography. Thermography relies on the fact that tumors tend to have higher temperatures than normal tissue due to the higher metabolic activity and vascularity of tumors. Therefore, the tumors tend to appear as hot spots in a thermogram of the breast. Thermography has definite advantages over mammography because it is non-invasive and non-hazardous both to the patients and to the personnel taking the thermograms.

The most common type of thermography is infrared thermography. Diagnostic techniques using electromagnetic emission in the infrared region of the spectrum have been available for many years and have proved useful in measuring surface temperature distributions in the body. However, body tissue rapidly absorbs electromagnetic energy at the infrared frequencies. Since the heat associated with a subcutaneous tumor is transferred by radiation as well as convection and conduction, the thermal pattern seen at the slain surface due to such a tumor can be altered significantly. In fact, in some cases, a relatively deep tumor may not appear at all in an infrared thermogram of the affected area. Thus, infrared thermography is essentially limited to surface measurements which can vary greatly in response to external factors such as physical activity, menstrual al cycle, substance intake, etc.

More recently there has been developed thermography systems for locating tumors in the body using microwave radiometry. These systems, which operate at the lower microwave frequencies, provide improved transmission characteristics in tissue and, therefore, allow detection at greater depths in tissue. Two such systems for detecting cancerous tumors are described in my U.S. Pat. Nos. 4,346, 716 and 4,774,961. Both of these systems screen for tumors by detecting radiometrically the increased energy emitted in the microwave band by the relatively hot cancerous tumors. The system described in the former patent utilizes a single relatively small detection antenna. Therefore, it is impractical for use in screening for breast tumors because it takes too long to probe all quadrants of the breast. The microwave detection apparatus described in the latter patent avoids this problem to some extent by employing a detection antenna array composed of a relatively large number (i.e., 6–12) of individual antennas which are switched, in turn, to a single radiometer. This allows the apparatus to image the entire breast, or at least a large area thereof, with each positioning of the apparatus relative to the breast.

When screening for breast tumors using the microwave radiometry system in my '961 patent, the usual procedure is to compare the temperatures at common locations on the two breasts of the patient to determine if there is a temperature difference. In other words, absent tumors, there is a surprising correspondence of temperatures at corresponding locations on opposite sides of a given individual, i.e., a temperature differential within about 0.2° C. Consequently, if a larger temperature differential does exist at corresponding locations on the two breasts, this is an indication that an abnormality may be present in the breast with the higher temperature reading. The usual practice, then, is to take temperature readings at various locations on one entire breast and then reposition the apparatus to take similar measurements at corresponding locations on the other entire breast. These readings are fed to a controller with data processing capability which compares them in order to produce a thermogram or other visual display showing the temperature differentials at the corresponding locations on the two breasts. Usually also, the temperature-indicating signals are processed using various known averaging, enhancement and target recognition techniques to increase the probability that a tumor-indicating hot spot will be recognized in the display.

When scanning for breast tumors using a multiple-antenna array according to the above procedure, it must be taken into consideration that an individual's breasts are handed. In other words, when facing an individual, the axillary gland area of the individual's right breast is to the left of the observer, while the axillary gland area of the individual's left breast is to the right of the observer. Therefore, if an antenna array is positioned against that individual's right breast, the antenna in the upper left corner of the array will be closest to the gland area of that breast. On the other hand, if the same array is pressed against that individual's left breast, the antenna in the upper right corner of the array will be closest to the gland area of that breast. This means that when temperature measurements are being taken of both breasts, the temperature information from the various antennas in the array being fed to the system controller must be switched so that proper comparisons are made of common points on the two breasts.

The multiple antenna arrangement described in my '961 patent is disadvantaged in that it requires breast compression so as to reduce the tissue thickness being examined in order to obtain accurate tissue temperature measurements of the breasts. In one embodiment of that patented system, a single multiple antenna array is held against the breast in order to compress the breast. In a second embodiment of that system, the breast is compressed between a pair of opposed multiple antenna arrays. In both cases, it has proven difficult to obtain the required intimate contacts between all of the antennas in the antenna array(s) and the surface of the breast for all areas of the breasts, with the result that sore& tumors may go undetected.

Also, when screening for tumors in relatively small breasts, in order to adequately compress the breast with the antenna array, the upper array has to be positioned so that, like the prior mammography systems described above, it may fail to detect tumors in the upper half of the breast and the axillary gland area above the breast.

Another disadvantage of having to compress the breast in order to screen for tumors is that the very act of compression upsets the blood circulation in the breast tissue and causes temperature changes therein. Therefore, after the antenna array(s) has been pressed against the breast, it is necessary to wait a couple of minutes to allow the breast temperature to stabilize before taking temperature measurements. This obviously increases the overall breast examination time. Also, the maintenance of the breast under compression causes discomfort to some patients and makes them more reluctant to undergo the breast screening procedure.

Further, in the prior multiple antenna detection systems described above, the individual antennas are arrayed in a stack or in offset courses like bricks in a wall. Resultantly, the array has a relatively large footprint or there may be gaps between the antenna patterns of the array which may allow some tumor-indicating hot spots to be missed during the breast examination.

Finally, the use of a multiple antenna array time-shared with a single radiometer introduces switching artifacts into the signals from the radiometer which can degrade the temperature readings obtained by the prior system.

For all of the above reasons, microwave radiometry is not as widely used to screen for breast tumors as might be expected considering the advantages which it offers in terms of detection penetration depth, safety and efficiency.

SUMMARY OF THE INVENTION

Accordingly, it is an object of the present invention to provide improved microwave radiometry apparatus for detecting tumors, particularly malignant breast tumors.

Another object of the invention is to provide such apparatus which facilitates making temperature comparisons at corresponding locations on a patient's two breasts.

Yet another object of the invention is to provide microwave detection apparatus which can screen for breast tumors in a minimum amount of time.

A further object of the invention is to provide apparatus of this general type which does not require compression of the breast during a breast examination.

Still another object of the invention is to provide microwave radiometry apparatus for screening for breast tumors which does not materially alter breast temperature during the screening process.

A further object of the invention is to provide apparatus of this type which includes a relatively small, hand-held, multiple antenna probe which can be positioned in intimate contact with all areas of the breast so as to accurately detect the temperatures thereat.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

In general, my detection apparatus includes a hand-held probe which may be positioned so that the working end of the probe makes intimate contact with a relatively large area of a patient's breast. Exposed at the working end of the probe is a compact array of microwave-receiving antennas which detects the electromagnetic energy in the microwave region emitted from tee tissue contacted by the probe. Each antenna includes a short section of rectangular waveguide, preferably dielectric loaded, which is coupled both mechanically and electrically directly to a dedicated radiometer also present in the probe. Thus, the temperature measurements for all antennas in the array are taken simultaneously.

The waveguide-radiometer pairs are oriented about the probe axis so that the end apertures of the waveguides are arranged in contiguous columns and rows at the working end of the probe and such that the aperture of each waveguide is oriented 90° relative to the aperture of any adjacent waveguide in the array. This produces an array which may be brought into contact with an appreciable area of the breast and yet one which has minimal gaps between the antenna patterns of the various antennas in the array. Resultantly, the probe, with each positioning, can obtain accurate temperature measurements, with a reasonable degree of resolution, from a relatively large continuous area of the breast so that an entire breast can be examined with minimum repositionings of the probe.

Preferably, all of the radiometers in the probe are mounted to a common thermally conductive fixture so that the radiometers make intimate thermal contact in exactly the same way with the fixture over relatively large surface areas so that there is a very uniform thermal distribution between the radiometers. The fixture thus functions as a heat sink to maintain all of tee radiometers at substantially the same temperature thereby stabilizing their gains assuring that they will take accurate temperature readings which will remain consistent over time. To further assure their stability, the radiometers are thermally insulated so they will not be affected by changes in the ambient temperature.

The temperature-indicating output signals from the radiometers, which comprise the output from the probe as a whole, are applied to a controller which processes the signals to produce digital data representing the temperatures of the areas of the breasts contacted by the probe. This data is used to control a monitor which may display the actual or relative temperatures at corresponding areas of the patient's breasts. The display may be in the form of a thermogram or some other temperature-indicating presentation such as one which color codes the different temperatures. In any event, the display will pinpoint the locations of any subcutaneous hot spots in the breasts that may be indicative of malignant tumors at those locations.

When screening for breast tumors with my apparatus, the procedure used is quite different from that described in my above-referenced '961 patent. Here, the patient is examined while lying supine on an examination table with the arms by the side with the hand on the hips to avoid the trapping of air at the breast areas. Then, using the probe, temperature measurements are taken at corresponding locations on the two breasts one right after the other. In other words, the working end of the probe may be placed over a selected location on the left breast and the microwave energy emitted thereat is received by each antenna in the probe and measured by the corresponding radiometer. The temperature information from each radiometer may then be stored in the controller and displayed if desired. Then, the examiner may position the probe at the corresponding location on the right breast and the temperatures at that location measured and stored in the same fashion. The apparatus controller may process the information using various averaging and signal recognition techniques to provide a temperature comparison of the two common breast locations. The examiner may then probe additional common areas of the two breasts one after the other in the same fashion. It is important to note that the probe is dimensioned so that its antennas can make intimate thermal contact with all breast sites appropriate for examination including upper half of the breast and the axillary gland area, even for those with small breasts.

When both breasts have been thermally mapped in their entireties, the examiner may cause the controller to store all the readings on a tape or disk so that the examination results for a given patient will be available for comparison with the results of a subsequent similar examination of that same patient.

An obvious advantage of this procedure is that the corresponding temperature measurements for the two breasts can be taken very close together in time thereby minimizing the chances of extraneous factors effecting the temperature measurements. More importantly, the examiner can obtain more information by making the temperature comparisons for each breast location substantially immediately. For example, the examiner may notice a slight temperature differential at corresponding locations on the two breasts which may provoke him or her to probe certain closely adjacent common locations on the two breasts to see if the temperature difference is greater or less at the latter common location. Following such "clues," the examiner may home in on a hot spot in one of the breasts. This would be impossible to do with the prior multiple antenna detection systems described above which take temperature measurements of the breast entireties before making any temperature comparisons.

As noted above, the placement of a probe against the skin can itself cause changes in the skin temperature thereby upsetting the radiometric temperature measurements. To avoid this problem, my apparatus may include an interface pad of low thermal mass between the working end of the probe and the skin area to be contacted. While the pad may be placed on the working end of the probe, it is more preferably a thin, mildly adherent insulating sheet placed over each of the patient's breasts which help to stabilize the breast surface temperature. As will be described in more detail later, these sheets may be marked with grids to facilitate proper placement of the probe at common locations on the two breasts to make the temperature comparisons described above.

Thus, using the present apparatus, one should be able to screen an individual for breasts tumors in no more time that it takes for a standard mammography examination. Furthermore with my apparatus, all areas of the breasts may be examined with equal facility thereby minimizing the likelihood that a subcutaneous tumor will be missed during the examination.

BRIEF DESCRIPTION OF THE DRAWINGS

For a fuller understanding of the nature and objects of the invention, reference should be had to the following detailed description taken in connection with the accompanying drawings, in which.

DESCRIPTION OF THE PREFERRED EMBODIMENT

Figure 1:
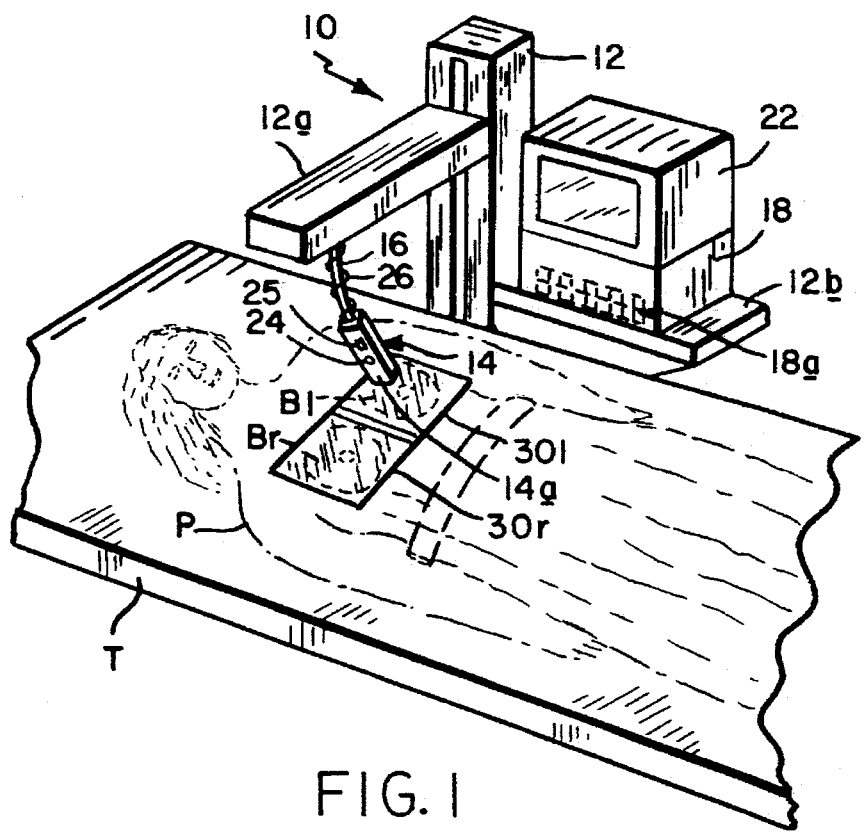
FIG. 1 is a fragmentary perspective view of microwave detection apparatus incorporating the invention being used to give a breast examination to a patient.

Referring to FIG. 1 of the drawings, my apparatus, shown generally at 10, is being used to conduct a breast examination of a patient P reposing in a supine position on an examination table T. The apparatus 10 includes a roll stand or wall bracket 12 which supports a vertically adjustable arm 12a that is arranged overhang table T. Suspended from arm 12a is a radiometric probe 14 having a working end 14a and which is electrically connected by an extensible cable 16 to a controller 18 having a control panel 18a. Controller 18 may be positioned on a platform 12b also supported by stand or bracket 12.

When the probe working end 14a is placed against the patient's breast $B_l$ or $B_r$, the probe will detect the thermoradiation emitted by the contacted breast area and emit corresponding electrical signals via cable 16 to controller 18. The controller may then cause a monitor 22, also supported by platform 12b, to provide a visual indication of the sensed temperatures. When the examiner is satisfied with the position of the probe, a control device such as a control button 24 on probe 14 may be depressed which sends a signal to the controller which causes the controller to store the temperature readings in a memory unit in the controller. Another control device such as a two-position switch 25 on probe 14 is present to allow the operator to tell the controller which breast is being probed to account for the fact that the breasts are handed as described above. Of course, the controls 24 and 25 could just as well be foot pedal switches or buttons on control panel 18a.

If desired, known means may be provided for counterbalancing probe 14. In the illustrated apparatus 10, these means comprise a coil spring 26 stretched between arm 12a and the probe 14. They could just as well be a pulley/counterweight arrangement in arm 12a. The counterbalance helps to minimize arm fatigue when an examiner has to manipulate the probe 14 for a prolonged period.

Also, thermally insulating interface pads $30_l$ and $30_r$ to be described in more detail later, may be present between the probe working end 14a and the breasts $B_l$, $B_r$ to stabilize the breast temperature and to prevent breast surface temperature change due to contact by the probe.

Figure 2:
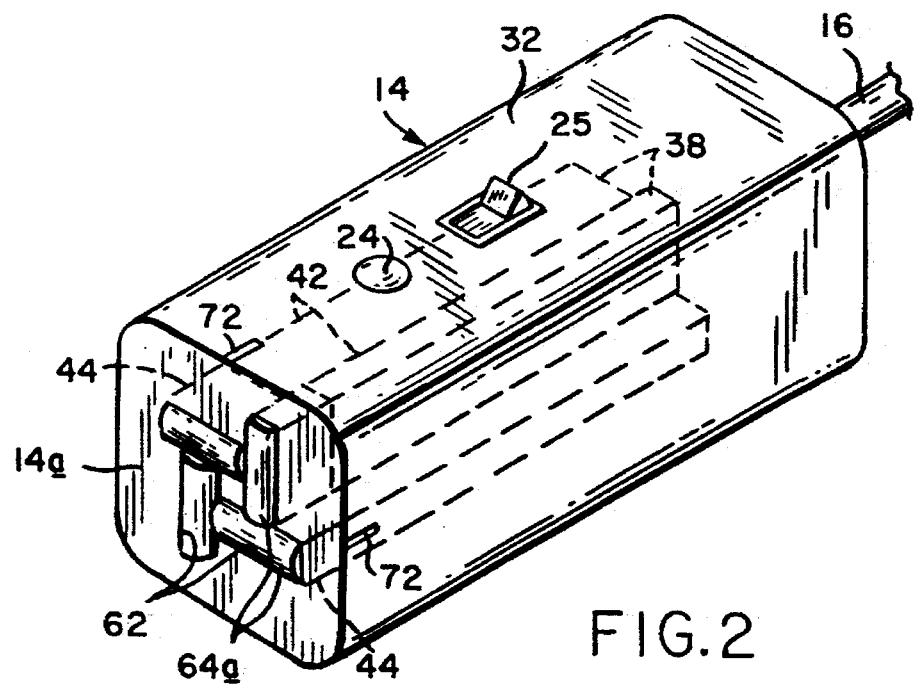
FIG. 2 is a perspective view on a much larger scale showing the radiometric probe component of the FIG. 1 apparatus.
Figure 3:
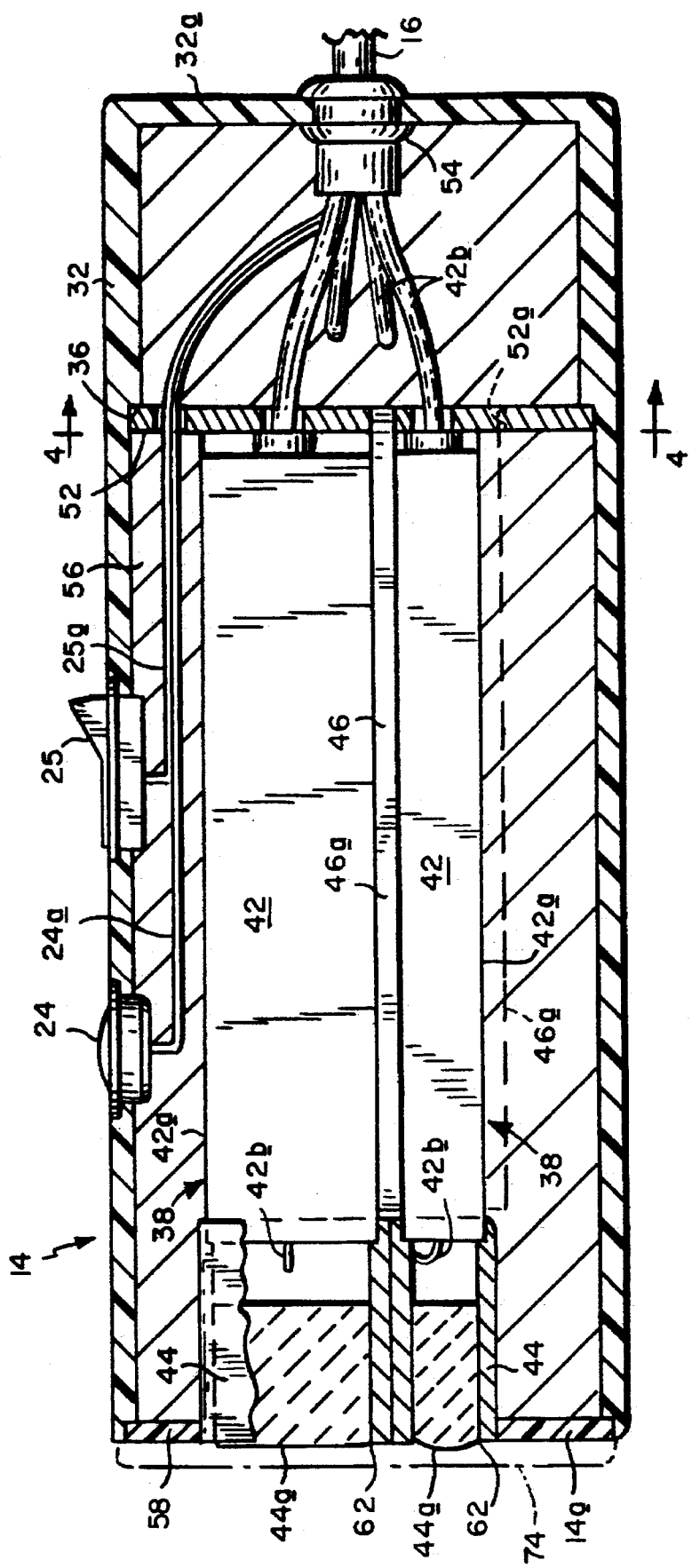
FIG. 3 is a sectional view on a still larger scale of the probe depicted in FIG. 2.
Figure 4:
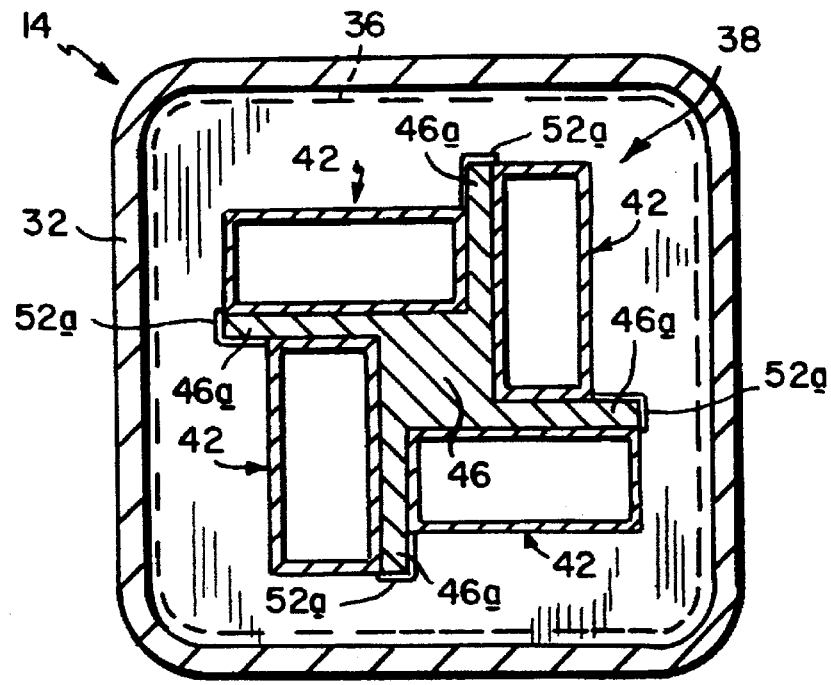
FIG. 4 is a sectional view taken along line 4—4 of FIG. 3.

Referring now to FIGS. 2 to 4 of the drawings, probe 14 comprises a generally cylindrical housing 32 preferably made of a suitable strong, impact resistant, electrically insulating plastic material. One end of housing 32 is closed by an end wall 32a; the other end of the housing is open. Also, a segment of the housing adjacent to end wall 32a may have a reduced internal diameter thereby forming an internal shelf 36 spaced from end wall 32a for reasons that will become apparent.

Housing 32 is designed to contain an array of substantially identical radiometric detection assemblies shown generally at 38. The illustrated probe 14 has four such assemblies. Each assembly comprises a generally rectangular radiometer 42 having a thermally conductive outer casing 42a and a coupling probe 42b extending from the outer end of the casing. Each assembly also includes an antenna in the form of a section of rectangular waveguide 44 telescoped onto, or otherwise connected to, the outer end of the radiometer so that the waveguide is coupled to the radiometer both mechanically and electrically via the former's coupling probe 42b.

The radiometer 42 of each assembly 38 is mounted directly to an elongated fixture 46 made of a thermally conductive material such as aluminum or copper metal. As shown in FIG. 3, fixture 46 is somewhat longer than radiometers 42 and, as seen in FIG. 4, it has a plurality, herein four, fins or blades 46a which extend out at right angles to one another. The fixture 46 supports each radiometer 42 such that all radiometer casings 42a are in intimate thermal engagement in exactly the same way with fixture 46 over large portions of the casings' surface areas. In other words, one broad wall of each casing 42a is opposite a narrow wall of an adjacent casing at all wall areas. This achieves a very uniform thermal distribution between the radiometers. Furthermore, for reasons that will become apparent, the fixture orients the detection assemblies 38 as a whole so that their waveguides 44 are arranged in contiguous columns and rows with the end aperture 44a of each waveguide being substantially perpendicular to and more or less bisecting the aperture of any adjacent waveguide 44 in the array.

As noted previously, fixture 46 may be somewhat longer than radiometers 42 so that it projects beyond the radiometers toward the housing end wall 32a. Its inner is keyed into slots 52a in a discoid bracket 52 which is arranged to seat on the internal shelf 36 of housing 32 so as to fix the positions of the inner ends of assemblies 38.

Each radiometer 42 has a multi-conductor cable 42 extending from the inner end of the radiometer. These cables are gathered together and pass through a grommet 54 mounted in the housing end wall 32a to become the probe's external cable 16. Also, the control buttons 24 and 25 have wires 24a and 25a which pass through grommet 54 into cable 16.

In order to thermally isolate the detection assemblies 38 from the environment, the remaining space inside housing 32 is preferably filled with a thermally insulating material 56 such as closed cell foam.

Referring now to FIGS. 2 and 3, the open end of housing 32 is closed by an end plate 58 which may be of the same material as housing 32. Plate 58 has an array of four contiguous rectangular openings 62 for snugly receiving the outer ends of the four waveguides 44, thereby fixing tile positions of the outer ends of the detection assemblies 38. Thus, the end plate 58 defines the working end 14a of probe 14.

The radiometer 42 comprising each detection assembly 38 is preferably of the Dicke switch-type. This radiometer design reduces the effects of short term gain fluctuations in the radiometer. The output of the radiometer is proportional to the temperature difference between associated waveguide 44 and a reference load in the radiometer. The design and operation of the radiometer is described in detail in my above U.S. Pat. No. 4,744,961, the contents of which are hereby incorporated herein by reference. A radiometer of this design suitable for use in apparatus 10 is available from Microwave Medical Systems, Inc., Acton, Massachusetts.

Since the radiometer per se does not constitute part of the present invention, it will not be detailed herein. Suffice to say that the radiometer has a bandwidth of about 500 MHz centered at 4.0 GHz. In use, the radiometer is maintained on standby so that it is heated by its internal elements to a temperature of about 34° C. But since all the radiometers are mounted to a common heat sink as noted above, they are all maintained at essentially the same temperature. Each radiometer has dimensions of about 10.2×3.8×1.5 cm. and each device weighs about 3 oz. so that an array of four detection assemblies 38 can be contained within a probe housing 32 that is in the order of 5.7 cm in diameter and 1.5 cm long, with the overall probe weighing under 20 oz. Thus, an examiner can easily manipulate the probe by hand when examining a patient.

Referring to FIG. 3 of the drawings, the waveguide 44 of each detection assembly 38 may be about 2.54 cm long and have a simple $TE_{10}$-mode aperture 44a designed to be in direct contact with the emitting surface, e.g., the surface of a breast $B_l$ or $B_r$ (FIG. 1). For dielectric loading purposes to reduce the physical size of the waveguide aperture 44a, a slab 64 of non-magnetic dielectric material may be located in each waveguide 44. A low-loss dielectric having a relative dielectric constant of about 9, e.g., aluminum oxide ceramic, may be employed, thereby providing an aperture size of about 3.10×1.55 cm. This aperture is slightly larger than the wavelength of the tissue contacted by the probe (e.g., about 3 cm at 4.0 GHz) which optimizes the antenna's detection penetration depth in the tissue.

In other words, when the aperture is matched to the tissue being contacted by the probe 14 as described, the antenna has maximum directivity and obtains maximum spatial resolution and tissue penetration. Furthermore, the tissue-air interface reflection at each antenna is minimized thereby providing maximum coupling of the emitted signal to the associated radiometer. Yet, an aperture of this size results in an antenna array which can still receive emissions from an acceptably large area of the breast with a single positioning Of the probe 14. In other words, the above described antenna array of four orthogonal waveguides produces a nice balance between the array's coverage on the tissue and its ability to penetrate the tissue with minimal gaps between the antenna patterns of the antenna array.

Figure 5:
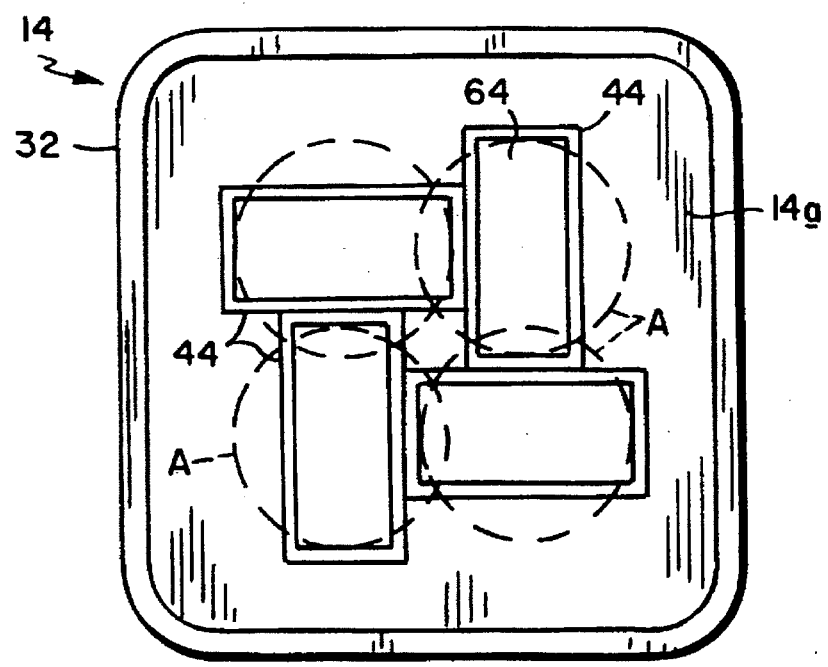
FIG. 5 is an end view of the FIG. 3 probe showing the receive patterns of the probe's antenna array.

This is illustrated in FIG. 5 which shows the roots of the antenna patterns A for the four waveguides 44 of probe 14. Each pattern has the general shape of a frustum of a cone whose diameter becomes progressively smaller with increasing distance from the aperture 44a of the associated waveguide. As seen from FIG. 5, the maximum diameters of the patterns A correspond to the widths of waveguides 44. Resultantly, the patterns of adjacent waveguides overlap and afford very uniform coverage of the tissue contacted by the working end 14a of probe 14.

As best seen in FIGS. 2 and 3, the outer surface 64a of each dielectric slab 64 is preferably domed so that it projects out slightly beyond the end plate 58. Thus, when the working end 14a of the probe is placed against a patient's breast during an examination, there will be no air pockets present between the ends of the waveguides 44 and the patient's skin that could degrade the temperature measurements taken by probe 14.

Figure 6:
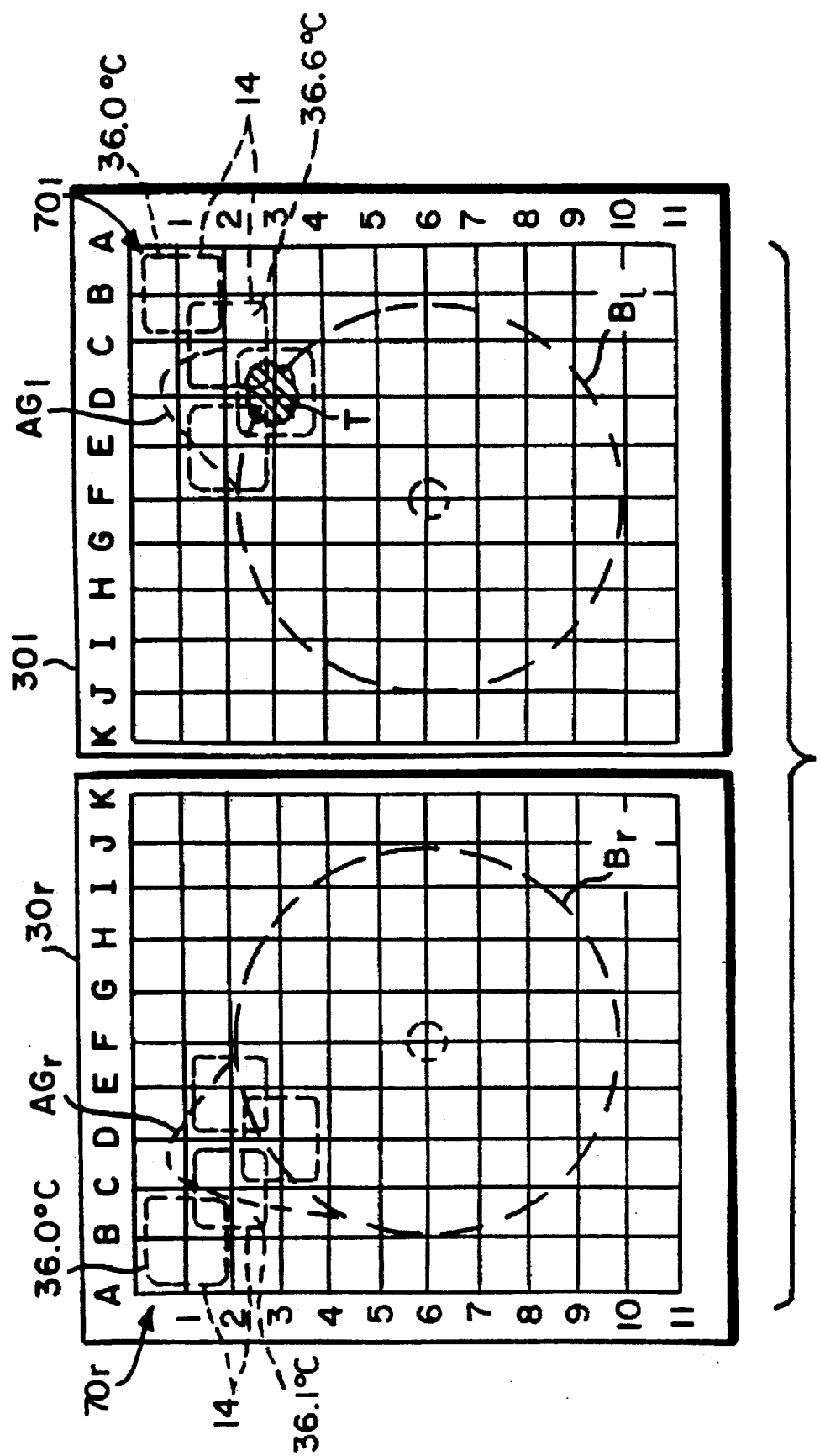
FIG. 6 is a plan view on a larger scale showing the interface pads that may be used with the FIG. 1 apparatus, which view also illustrates the use of that apparatus.

Refer now to FIG. 6 which illustrates the interface pads 30$_r$ and 30$_l$ in greater detail. Each pad is basically a thin (e.g. 0.12 cm) sheet of a thermally insulating material such as closed cell foam. The pads are sized to cover the breasts B$_r$ and B$_l$ and the areas around the breasts including the axillary gland areas AG$_r$ and AG$_l$. The pads 30$_r$, 30$_l$ may be contoured to some extent so that they conform more or less to the shape of the breast and preferably their undersides are covered with a release adhesive so that the pads may be mildly adhered to a patient's chest as shown in FIG. 1. When so applied, the interface pads insulate the breast areas from the atmosphere so that their surface temperatures are stabilized. Also, when the probe 14 is placed against a breast during an examination, the overlying pad isolates that breast so that contact by the probe 14 does not alter the surface temperature of the contacted area of the breast. Therefore, it is not necessary to wait at all before a temperature reading can be taken at that breast area.

Preferably also, the pads 30$_r$ and 30$_l$ carry grids 70$_r$ and 70$_l$, respectively, to facilitate targeting selected areas of the underlying breasts. As illustrated in FIG. 6, each grid may include lettered columns and numbered rows of lines. Preferably, the grids are mirror images of one another so that common points on the two breasts may be designated by the same letter and number on the two grids. Thus, when comparing the temperatures at corresponding locations on the two breasts using probe 14, the working end 14a of the probe may be positioned opposite a selected lettered column and numbered row of each grid. To facilitate such placement, benchmarks 72 may be inscribed 90° apart on the probe housing 32 adjacent to the working end of the probe as shown in FIG. 2. Thus, when examining a patient, the examiner may line up the bench marks 72 with the grid lines on the two interface pads 30$_r$, 30$_l$ which will ensure that common locations on the two breasts are being probed as the temperature comparisons are being developed.

Instead of using the interface pads 30$_l$ and 30$_r$, a single interface pad may be affixed to the working end 14a of probe 14 as shown in phantom at 74 in FIG. 3. Pad 74 would also serve to insulate the contacted area of the breast from the probe. However, the pad 74 would obviously not help to stabilize the surface temperatures of the breasts as do pads 30$_l$, 30$_r$.

When examining a patient P (FIG. 1), the examiner might start by positioning probe 14 at location B1 of pad 30$_r$, as shown in FIG. 6, after setting switch 25 to its "right" position so that the controller 18 knows that the right breast is being probed. When the examiner is satisfied the position of the probe, the control button 24 may be depressed so that the signals from the four radiometers 42 representing the temperatures at the breast areas contacted by the four antennas 44 are logged into the controller's memory.

Then, after setting switch 25 to its "left" position, the examiner may place probe 14 opposite the corresponding area B1 on the left breast and, by depressing switch 24, store the four temperature readings from that location in the controller 18 in the same way. The controller processes the temperature data at the two locations and the temperatures may be displayed by the monitor 22. The visual presentation may be actual temperature numbers overlaid on a visual display such as FIG. 6. Alternatively, the different temperatures may be displayed in different colors by the monitor 22. Also, controller 18 may be programmed to use various known signal recognition and enhancement techniques so that when one of the detection assemblies 38 in probe 14 detects an area of the breast that is significantly hotter than the breast areas under the other three assemblies 38 of the probe, an enhanced output from that one assembly 38 will readily be apparent in the monitor display. In the example in FIG. 6, the average temperatures detected at locations B1 on the two breasts are displayed and shown as 36.1° C. and 36.0° C., respectively. Therefore, the first temperature comparison shows no hot spot.

The examiner may then move the probe 14 to a second location on the right breast, say, to the position C2, and log the four temperature readings at that location into the controller 18, i.e., average temperature 36.1° C. The examiner then places the probe 14 opposite the corresponding location C2 on the left breast and the four temperatures at that location are detected by the assemblies 38 and logged into the controller. At that location, apparatus 10 detects an elevated average temperature of 36.6° C. indicating that a tumor may exist in the left breast B$_l$ near that location. The examiner may then probe other common areas of the two breasts, such as location E2, to develop other temperature comparisons. Following successive comparisons, the examiner will be able to home in on the location of the tumor T at position D3 on the left breast.

The controller 18 can also process the signals from probe 14 in other ways such as by comparing the temperature detected by each probe assembly 38 with the average of the temperatures detected by the other three assemblies to avoid the effect of cold spots in the temperature measurements. Further, the patient may be given a vasoconstrictor, such as phenylephrine hydrochloride, so that a hot spot due to a tumor will stand out against the temperature of normal tissue. This is possible because the vasoconstrictor tends to reduce the temperature of the tissue surrounding a tumor but not the tumor itself due to the fact that a tumor has its own vasculature which is relatively unaffected by the vasoconstrictor.

It will thus be seen that the objects set forth above, among those made apparent from the preceding description are efficiently attained. Also, certain changes may be made in the above construction without departing from the scope of the invention. For example, the apparatus may be used to probe for subcutaneous malignant lesions other than breast tumors. Also, in some cases, the radiometers 42 may be in direct heat exchange contact thereby avoiding the need for fixture 42. In that event, the apparatus will still have many of the advantages described above. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. Microwave tumor detection apparatus comprising a probe having a working end for contacting tissue, and a plurality of rectangular waveguides positioned in an array of columns and rows within said probe, each waveguide having an aperture at the working end of the probe which is oriented perpendicular to the aperture of the waveguide in any adjacent column and row of the array, each waveguide constituting an antenna tuned to receive thermoradiation emitted from tissue opposite the working end of the probe.

2. The apparatus defined in claim 1 and further including detection means coupled electrically from said waveguides for detecting said thermoradiation and determining therefrom the temperature of tissue opposite the working end of the probe.

3. The apparatus defined in claim 1 wherein a segment of each waveguide adjacent to the working end of the probe is filled with a slab of non-magnetic dielectric material for dielectric loading purposes.

4. The apparatus defined in claim 1 wherein said waveguide array comprises two columns and two rows of waveguides.

5. Microwave tumor detection apparatus comprising a probe having a working end for contacting tissue, a plurality of rectangular waveguides positioned in an array of columns and rows within said probe, each waveguide having an aperture at the working end of the probe which is oriented perpendicular to the aperture of the waveguide in any adjacent column and row of the array, each waveguide constituting an antenna tuned to receive thermo-radiation emitted from tissue opposite the working end of the probe, and detection means coupled electrically from said waveguides for detecting said thermo-radiation and determining therefrom the temperature of tissue opposite the working end of the probe, said detection means comprising a corresponding plurality of radiometers in said probe, each radiometer being coupled both mechanically and electrically to a different waveguide of the waveguide array.

6. The apparatus defined in claim 5 wherein each radiometer has a thermally conductive exterior casing, and further including means thermally connecting together all of said casings so that all of the radiometers have a uniform thermal distribution.

7. The apparatus defined in claim 6 wherein said connecting means include a thermally conductive fixture in said probe, and means for maintaining said casings flush against said fixture so that all of the radiometers are in thermal equilibrium with the fixture.

8. The apparatus defined in claim 7 and further including thermal insulation surrounding said radiometers in said probe.

9. The apparatus defined in claim 5 wherein each waveguide is engaged to the corresponding radiometer and the corresponding radiometer includes a coupling probe which projects into the engaging waveguide to effect their electrical coupling.

10. Microwave tumor detection apparatus comprising a probe having a working end for contacting tissue, a plurality of rectangular waveguides positioned in an array of columns and rows within said probe, each waveguide having an aperture at the working end of the probe which is oriented perpendicular to the aperture of the waveguide in any adjacent column and row of the array, each waveguide constituting an antenna tuned to receive thermo-radiation emitted from tissue opposite the working end of the probe, and a thermally insulated interface pad positioned between the antenna apertures and any tissue opposite the working end of the probe.

11. The apparatus defined in claim 10 wherein said pad is affixed to the working end of the probe.

12. The apparatus defined in claim 10 wherein said pad is arranged and adapted to be affixed to tissue opposite the working end of the probe.

13. The apparatus defined in claim 12 and further including a grid inscribed on said pad for designating locations on underlying tissue.

14. Microwave tumor detection apparatus comprising probe having a working end for contacting tissue, and a plurality of rectangular waveguides positioned in an array of columns and rows with said probe, each waveguide having an aperture at the working end of the probe which is oriented perpendicular to the aperture of the waveguide in any adjacent column and row of the array, each waveguide constituting an antenna tuned to receive thermo-radiation emitted from tissue opposite the working end of the probe, a segment of each waveguide adjacent to the working end of the probe being filled with a slab of non-magnetic dielectric material for dielectric loading purposes, the slab in each waveguide being shaped to form a dome which projects slightly beyond the aperture of the corresponding waveguide.

15. Microwave tumor detection apparatus comprising a probe having a working end for contacting tissue; a plurality of microwave antennas positioned at the working end of said probe; detection means coupled from said antennas for detecting the temperature of tissue opposite the working end of the probe, and a thermally insulating interface means positioned between the antennas and tissue opposite the working end of the probe.

16. The apparatus defined in claim 15 wherein said interface means comprise a thin pad arranged and adapted for fixation affixed to the working end of the probe.

17. The apparatus defined in claim 15 wherein said interface means comprise a thin pad affixed to tissue opposite the working end of the probe.

18. The apparatus defined in claim 15 and further including a grid inscribed on said pad for designating locations on underlying tissue.

19. The apparatus defined in claim 15 wherein said detection means comprise a corresponding plurality of radiometers in said probe, each radiometer being coupled electrically from a different antenna of the antenna array.

20. The apparatus defined in claim 19 wherein said antennas comprise rectangular waveguides and said radiometers include coupling probes which project into the corresponding waveguides.

21. Microwave tumor detection apparatus comprising a probe having a working end for contacting tissue; a plurality of microwave antennas positioned at the working end of said probe; a corresponding plurality of radiometers positioned in said probe, each radiometer being coupled electrically from a different antenna of the antenna array and including a thermally conductive casing, and means thermally connecting together all of said casings so that all of the radiometers have a uniform thermal distribution.

22. The apparatus defined in claim 21 wherein said thermally connecting means include a thermally conductive fixture positioned in said probe, and means for mounting all of said castings flush to said fixture so that all of said radiometers are in thermal equilibrium with said fixture.

23. The apparatus defined in claim 22 and further including thermal insulation surrounding said radiometers in said probe.

24. The apparatus defined in claim 22 wherein there are four radiometers in said probe, and said fixture comprises four elongated generally rectangular blades connected together on edge along their lengths so that the fixture has a longitudinal axis, said blades being distributed 90° apart about said axis and being at least as long as said radiometers.

25. Microwave tumor detection apparatus comprising a probe having a working end for contacting tissue;
 a plurality of rectangular waveguides positioned in an array of columns and rows within said probe, each waveguide constituting an antenna tuned to receive thermo-radiation in the microwave region of the spectrum emitted from tissue opposite the working end of the probe;

a corresponding plurality of radiometers in said probe, each radiometer including a thermally conductive exterior casing and being coupled both mechanically and electrically to a different waveguide of the waveguide array;

means thermally connecting together all of said casings so that all of the radiometers have a uniform thermal distribution, and a thermally insulating interface pad positioned between the antenna apertures and any tissue opposite the working end of the probe.

26. The apparatus defined in claim 25 and further including a slab of non-magnetic dielectric material positioned in each waveguide for dielectric loading purposes.

27. The apparatus defined in claim 25 and further including thermal insulation surrounding said radiometers in said probe.

28. The apparatus defined in claim 27 and further including a grid inscribed on said pad for designating locations on underlying tissue.

* * * * *